United States Patent [19]

Sugai et al.

[11] 4,189,836
[45] Feb. 26, 1980

[54] CHUCK FOR DENTAL HAND-PIECE

[75] Inventors: Hiroshi Sugai; Haruo Ogawa, both of Higashihama Minami, Japan

[73] Assignee: Kabushiki Kaisha Morita Seisakusho, Kyoto, Japan

[21] Appl. No.: 921,230

[22] Filed: Jul. 3, 1978

[30] Foreign Application Priority Data

Jul. 4, 1977 [JP] Japan .......................... 52/88985[U]

[51] Int. Cl.² .............................................. A61C 1/12
[52] U.S. Cl. .................................. 433/127; 279/1 G; 433/134
[58] Field of Search ..................... 32/26, 27; 279/1 G, 279/52

[56] References Cited

U.S. PATENT DOCUMENTS

| | | | |
|---|---|---|---|
| 3,324,553 | 6/1967 | Borden | 32/27 |
| 3,325,899 | 6/1967 | Staunt | 32/27 |
| 3,962,789 | 6/1976 | Flatland | 32/27 |

Primary Examiner—Robert Peshock
Attorney, Agent, or Firm—Koda and Androlia

[57] ABSTRACT

A cartridge-type chuck for use in a dental handpiece wherein a substantially cylindrical cartridge case incorporates within itself at least a friction-type chuck body and a stopper provided with a square hole of a smaller diameter than the inner diameter of said chuck body, said cartridge case being formed at its front part into truncated cone by tapering the outer circumferential surface and is provided at its thickened rear part with a threaded interface on the circumference, is disclosed. This cartridge-type chuck is able to be loaded and unloaded for the purpose of replacing it with ease in relation to the rotor disposed in the inside of a dental handpiece, into which the dental cutting tool can be inserted by a single step, and whose holding power is strong enough to be free from occurrence of the center whirling of the spindle of said cutting tool.

3 Claims, 4 Drawing Figures

4,189,836

CHUCK FOR DENTAL HAND-PIECE

BACKGROUND OF THE INVENTION

1. Field of the Invention

This invention relates to a novel cartridge-type chuck for use in a dental hand-piece, and particularly to a cartridge-type chuck which is easy and simple for any person to attach and detatch for the purpose of exchange in relation to a rotor arranged in the interior of a hand-piece and which is free from the occurrence of center whirling of the dental cutting tool that is to be inserted thereinto.

2. Prior Art

As is well known in the field of the dental hand-piece, various types of chucks have been developed and broadly used. But as for the chuck, needless to say, it is desirable to be of good operability and durability, and also to be easily changeable for the dentist or user with his own hands.

Conventional chucks, however, have suffered from such defects that they are not exchangeable outside of special workshops with the exception of what is called a plastic (vinyl) chuck. But this plastic chuck itself has also a fatal flaw that its life-time is short, setting aside the question of the exchangeability. Such being the case, the state of things is eagerly anticipating the appearance of such a kind of chuck that can be easily exchanged by the hand of the user, and that may have a great holding power so as to prevent it from the center whirling of its spindle.

SUMMARY OF THE INVENTION

The present invention has been contrived in the light of the above-mentioned situation. It has for its object to provide a cartridge-type chuck which is able to be loaded and unloaded for the purpose of replacing it with easiness in relation to the rotor disposed in the inside of a dental hand-piece, into which the dental cutting tool can be inserted by a single step, and whose holding power is strong enough to be free from the occurrence of the center whirling of the spindle of the said cutting tool.

The invention will be elucidated more fully with reference to a preferred embodiment of the cartridge-type chuck according to the present invention shown in the drawing.

DETAILED DESCRIPTION OF THE INVENTION

Figure 1:
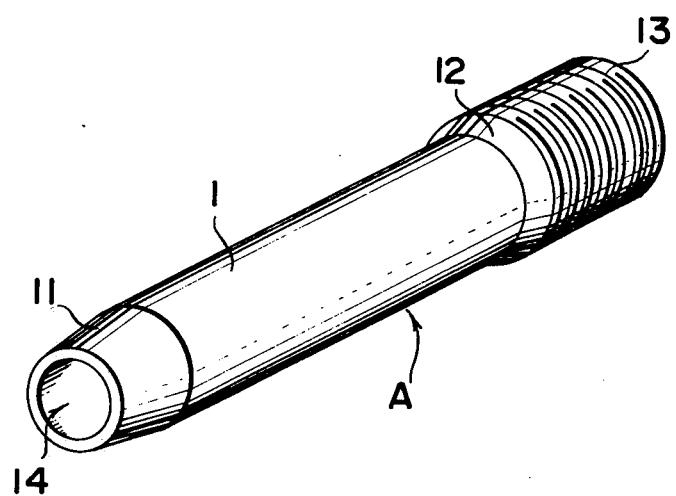
FIG. 1 is a perspective view showing an embodiment of the cartridge-type chuck according to the present invention.
Figure 2:
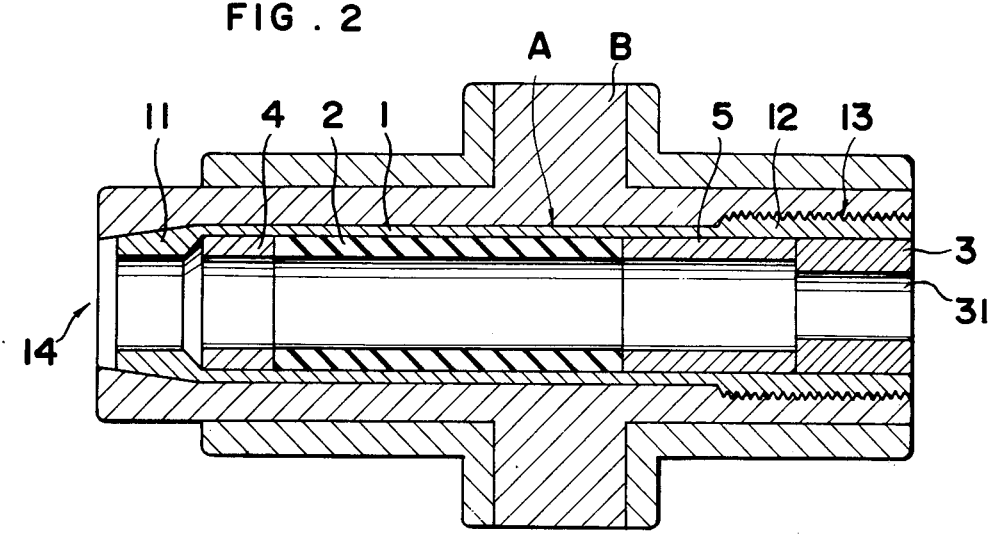
FIG. 2 is a longitudinal sectional view showing the chuck of FIG.1 in a state where it has been screwed-in and tightly secured within the rotor.

As seen in FIG. 1, the cartridge-type chuck according to the present invention has an appearance of a substantially cylindrical shape, and, as seen in FIG.2, a substantially cylinder-shaped cartridge case 1 incorporates within itself at least a friction-type chuck body 2 and a stopper 3, both pressed-in and fixed therein, and further it is preferable that said cartridge case 1 includes a front collar 4 and rear collar 5 at its front part and at its rear part, respectively, of the friction-type chuck body 2. On the other hand, the aforesaid cartridge case 1 is constructed in such a manner that it is formed at its front end 11 into a truncated cone by tapering the outer circumferential surface thereof and at its thickened rear end 12 with a threaded interface 13 on the circumference thereof.

Figure 3A:
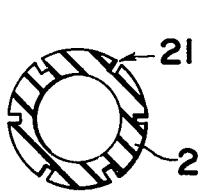
FIGS. 3(a) and 3(b) are a cross sectional view in the radial directon and a longitudinal sectional view in the axial direction, respectively, of the friction-type chuck body for use in the present invention.
Figure 3B:
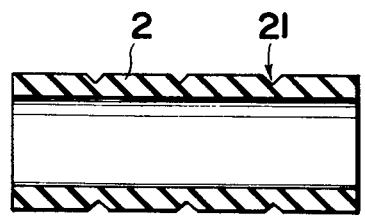

The friction-type chuck body 2 here is made, for example, out of an elastic material such as polyurethane that is of high elasticity, resistance to wear, and coefficient of friction, and is provided, as shown in FIGS. 3(a) and 3(b), on its outer surface with a plurality of slots 21 in the axial and/or radial directions, a feature which causes the expansion of the chuck 2 to be efficiently absorbed at the time of inserting the spindle of the dental cutting tool (not shown) thereto through the opening 14 at the front end of the cartridge case 1, in consequence of which the insertion resistively of the spindle is able to be kept approximately constant, irrespective of some difference in the diametral length thereof.

As for said stopper 3, it is pressed-in through the opening at the rear end of the cartridge case 1 and fixedly secured thereat in order to prevent the inserted cutting tool from passing through backward, for the purpose of which a square hole 31 of a smaller diameter than the inner diameter of the chuck body 2 is perforated therethrough (the hole in the illustration is square in section, but other polygonal holes than this are of course adoptable), and this square hole 31 is so constructed that a suitable implement can be put therein with a view to screwing the whole cartridge case 1 on and back, thereby the cartridge-type case 1 being able to be easily loaded and unloaded in relation to the rotor B having in its inner face the form and threaded interface correspondent to those of the outer face of the said case 1.

If the cartridge case 1 and the inner wall of the rotor B draw extremely near to each other, the exchange operation of the cartridge case becomes difficult. The design is, therefore, wont to be worked out so as to be able to produce a clearance, though to a very small extent, between them. In the present invention, however, the problem of the center whirling raised by the presence of such a minute clearance or by the existence of the threaded interface between them has been settled by such a contrivance as to force the front part 11 of the cartridge case to closely touch with the inner wall of the rotor B concentrically through tapering the said front part 11 to be formed into a truncated cone. In this way, the most distinctive feature of the present invention which was never seen in conventional chucks resides in the wholly exceeding novelty of the contrivance wherein the cartridge case 1 is formed at its front part 11 into a truncated cone to prevent the spindle of the cutting tool inserted therein from the center whirling, and, on the other hand, it is argumented in thickness at its rear part 12 to form the threaded interface 13 on the circumference thereof, thereby leading to the easy and simple exchangeability of the chuck itself.

It is to be noted that in the cartridge-type chuck a front collar 4 and a rear collar 5 are preferably incorporated together before and behind the friction-type chuck body 2. These two collars are provided for the restriction of the whirling of the spindle of the cutting tool due to the centrifugal force created by the 300,000 to 500,000 r.p.m. of the cartridge-type chuck A according to the present invention as the rotor B rotates, and besides they aim at the enhancement of the life expectancey of the chuck.

The cartridge-type chuck of such a construction, as described above according to the present invention, incorporates within itself the friction-type chuck body 2 made of an elastic body provided with the plurality of slots in its radial and/or axial directions, in consequence of which the cutting tool can be inserted thereinto at one touch at an approximately constant force regardless of some difference in the diametrical length of the spindle of the cutting tool with no fear of slipping out by dint of a great holding power of the chuck body 2, while the loading and unloading operation for exchanging the cartridge case 1 can be easily conducted by the hand of the user only by screwing up and back the whole cartridge case 1 in and from the inside of the rotor B with the use of a suitable implement inserted into the square hold 31 of the stopper 3, and therewith the perfectly concentric loading of the chuck body 2 with the cartridge case 1 is made possible by the action of the truncated cone-shaped front part of the latter 1 so as not to cause the center whirling of the cutting tool to occur. These and many other remarkable effects can be exhibited by the present invention. It may be given as a conclusion that the present invention has a great deal of high practicability.

We claim:

1. A chuck adapted to be snug fit into the rotor of a dental hand-piece comprising:
    a substantially cylindrical cartridge case having an inner diameter formed to hold a chuck body and a stopper snug fit to said inner diameter of said cartridge case, said cartridge case having a tapered portion in the form of a truncated cone on the outer circumferential surface at one end thereof and a threaded, thickened outer circumferential surface at the opposite end thereof to enable said cartridge case to be snug fit into the rotor;
    a chuck body having an inner diameter and adapted to securely engage the spindle of a dental tool within said inner diameter of said chuck body, said chuck body being snug fit to the inner diameter of said cartridge case;
    front and rear collars each having an inner diameter equal to said inner diameter of said chuck body and each snug fit to the inner diameter of said cartridge case at opposite ends of said chuck body, said front and rear collars being adapted to securely engage the spindle of a dental tool within the inner diameters of said collars; and
    a stopper having a square cross-sectional inner surface and having a smaller diameter than the inner diameter of said chuck body, said stopper being securely fitted to the inner diameter of said cartridge case at the end opposite the tapered end to thereby provide a stop for the spindle of a dental cutting tool.

2. The apparatus as described in claim 1 and wherein said chuck body is a cylindrical elastic body having a plurality of slots in its outer circumferential surface in the axial and radial directions.

3. The appratus as described in claim 2 and wherein said chuck body is formed of polyurethane.

* * * * *